(12) United States Patent
Brunel

(10) Patent No.: US 7,312,868 B2
(45) Date of Patent: Dec. 25, 2007

(54) METHOD AND DEVICE FOR MEASURING A LIGHT FLUX BACKSCATTERED BY A DISPERSED MEDIUM, UNPERTURBED BY INTERFACE REFLECTIONS

(75) Inventor: Laurent Brunel, Peyrins (FR)

(73) Assignee: Formulaction, L'Union (FR)

( * ) Notice: Subject to any disclaimer, the term of this patent is extended or adjusted under 35 U.S.C. 154(b) by 246 days.

(21) Appl. No.: 10/519,460

(22) PCT Filed: Jun. 25, 2003

(86) PCT No.: PCT/FR03/01959

§ 371 (c)(1),
(2), (4) Date: Dec. 29, 2004

(87) PCT Pub. No.: WO2004/005897

PCT Pub. Date: Jan. 15, 2004

(65) Prior Publication Data

US 2006/0061766 A1    Mar. 23, 2006

(30) Foreign Application Priority Data

Jul. 2, 2002    (FR) .................................. 02 08235

(51) Int. Cl.
*G01N 21/00*    (2006.01)
(52) U.S. Cl. ..................................... 356/342
(58) Field of Classification Search ............... None
See application file for complete search history.

(56) References Cited

U.S. PATENT DOCUMENTS 3,843,268 A    10/1974    Kaye 5,833,344 A * 11/1998 Arai et al. ................... 362/620
6,100,541 A    8/2000 Kennedy et al.
6,290,364 B1 * 9/2001 Koike et al. ................ 362/620

FOREIGN PATENT DOCUMENTS

EP    0 404 258    12/1990
EP    0 447 991    9/1991

\* cited by examiner

*Primary Examiner*—Tu T. Nguyen
(74) *Attorney, Agent, or Firm*—Young & Thompson

(57) ABSTRACT

A method for measuring a light flux backscattered by a dispersed medium located on one first side of a wall, by interaction with a plurality of light rays emitted from the second opposite side of the wall where the dispersed medium is located and towards the latter, the plurality of light rays being adapted to pass through the wall and being backscattered at least partly by the dispersed medium towards reception elements arranged on the second side of the wall. The method includes: emitting the plurality of light rays towards the dispersed medium and through the wall so as to form a backscattering spot having a central disc whose center corresponds to the luminous barycenter of the spot and whose radius is equal to four times the maximum free travel path (1*max) of the dispersed medium.

29 Claims, 5 Drawing Sheets

METHOD AND DEVICE FOR MEASURING A LIGHT FLUX BACKSCATTERED BY A DISPERSED MEDIUM, UNPERTURBED BY INTERFACE REFLECTIONS

FIELD OF THE INVENTION

The present invention relates to a method and a device for measuring a light flux backscattered by a dispersed medium located on a first side of a wall, by interaction with a plurality of light rays emitted from the second side of said wall which is opposite the first side, where said dispersed medium is located and in the direction of the latter, said plurality of light rays being able to traverse said wall and being backscattered at least partially by said dispersed medium in the direction of receiving means located on the second side of the wall; as far as the device is concerned, said wall being able to be traversed by said emitted and backscattered light rays and to be in contact with said dispersed medium.

BACKGROUND OF THE INVENTION

Prior art teaches such a method and device. Radiation backscattered by the dispersed medium in the form of a light flux traverses the separating wall between the dispersed medium and the receiver of the light flux backscattered by said dispersed medium, before reaching said receiver; and as a result, the applicant has confirmed that said wall reflects a part of the light rays backscattered by the dispersed medium, and sends them back into the latter, these reflected rays being able then to be backscattered once again by the medium in the direction of the wall and being able to reach the receiver of the light flux located on the other side of this wall, inducing perturbations of the light flux backscattered by the dispersed medium with respect to the emitted light flux, and as a result, measurement errors of the light flux backscattered by the dispersed medium. In fact, the analysed dispersed medium is in general of a higher optical index than that of air and lower than that of the material forming the wall. Furthermore, the light rays reemitted by the medium can demonstrate very inclined exit angles. Calculation models using the measurement of the backscattered light flux do not take into account those light rays reemitted by the medium.

FIG. 1 illustrates the problem of light rays reflected by the wall and reemitted by the medium. The medium 1 comprises for example particles 2 on which the light rays are diffused; certain rays 4 backscattered by the medium traverse the wall 3 in order to form the backscattered light flux which is to be measured, whilst other backscattered light rays 5, instead of traversing the wall 3, are reflected by the latter and sent back into the medium 1 which can reemit them at another position so that they are added to the backscattered light flux, therefore perturbing in particular its distribution. The reference 6 illustrates the backscattering spot which forms the backscattered light flux. FIG. 2 shows a distribution 7 in fine lines, which is radial according to the radius ρ of the light flux F in the backscattering spot, in which the perturbation 8 caused by the light rays reemitted by the medium is presented in thick lines. It is confirmed that this perturbation 8 is not negligible taking into account its large amplitude.

SUMMARY OF THE INVENTION

The present invention allows these disadvantages to be reduced. More precisely, it relates to a method for measuring a light flux backscattered by a dispersed medium located on a first side of a wall, by interaction with a plurality of light rays emitted from the second side of said wall which is opposite the first side, where said dispersed medium is located and in the direction of the latter, said plurality of light rays being able to traverse said wall and being backscattered at least partially by said dispersed medium in the direction of receiving means located on the second side of the wall, characterised in that said method comprises at least the following steps:

emitting said plurality of light rays in the direction of said dispersed medium and through said wall so that said dispersed medium is able to emit in turn, through said wall, a plurality of backscattered light rays with the aim of forming a backscattering spot in which at least one central zone in the form of a disc is defined, the centre of which corresponds to the luminous barycentre of the backscattering spot and the radius of which is equal to four times the maximum free transport length ($1^*_{max}$) of said dispersed medium, said backscattering spot being able to be imaged at least in part on said receiving means, forming said backscattering spot from backscattered light rays which have traversed said wall and are free, at least according to a direction extending from the luminous barycentre of said spot, of light rays which have emanated from said central zone and have undergone a total reflection on the surface forming the interface of said wall with said second side, measuring at least one spatial sample of a profile of the light flux in said thus obtained backscattering spot, extending in said at least one direction.

The method according to the invention allows, thanks to the suppression in the backscattering spot of the light rays which have emanated from said central zone and have undergone a total reflection, provision of an unperturbed light flux, and therefore a more precise measurement, more reliable than the mathematic model or models which will be able to be used in order to characterise the dispersed medium.

According to a feature, the method according to the invention comprises:

forming said backscattering spot from backscattered light rays which have traversed said wall and are free, between two directions extending from the luminous barycentre of said spot, of light rays which have emanated from said central zone and have undergone a total reflection on the surface forming the interface of said wall with said second side, measuring at least one spatial sample of a profile of the light flux in said thus obtained backscattering spot, extending at least over a surface defined between the two said directions which intersect at said luminous barycentre.

According to another feature, the method according to the invention comprises furthermore determining the values of the free transport length $1^*$ and the absorption length $1_a$ using a determined photon-dispersion interaction model, from said spatial sample of a profile of the light flux.

There is understood by photon-dispersion interaction model any theorem allowing the interaction of the light with the medium into which it is sent to be modelled.

According to another feature, the method according to the invention comprises avoiding the return into said dispersed medium of light rays which have emanated from said central zone and have undergone a total reflection on the surface forming the interface of said wall with the second side.

This feature comprises diverting the light rays which have emanated from total reflections out of the dispersed medium so that these reflected rays no longer perturb the distribution of the light flux into the latter, and do not modify the light flux in the backscattering spot.

According to another feature of the former, the method according to the invention comprises associating a first surface forming the interface of said wall with said first side, with a second surface forming the interface of said wall with said second side, said first and second surfaces being parallel.

According to another feature of the former, the usable half-width of said wall is less than or equal to twice the thickness of said wall minus four times the maximum free transport length $1^*_{max}$ of said dispersed medium.

According to another feature, the method according to the invention comprises associating a first surface forming the interface of said wall with said first side, with a second surface forming the interface of said wall with said second side, said first and second surfaces being non-parallel.

According to another feature, said first surface forming the interface of said wall with said first side is curved, and said second surface forming the interface of said wall with said second side is flat.

According to another feature, said first surface forming the interface of said wall with said first side is cylindrical.

According to another feature, said first surface forming the interface of said wall with said first side is flat, and said second surface forming the interface of said wall with said second side is concave.

According to another feature of the former, said second surface forming the interface of said wall with said second side is conical or truncated.

According to another feature, the method according to the invention comprises avoiding the total reflection of a light ray which has emanated from the central zone and has undergone a total reflection on the surface forming the interface of said wall with the second side, through which the backscattered light rays pass which are intended to form said backscattering spot.

This feature comprises preventing the formation of light rays which emanate from said central zone and are able to undergo a total reflection in order that the latter do not perturb the distribution of the light into the medium, and do not modify the light flux in the backscattering spot.

According to another feature, the formation of a light ray which has emanated from said central zone and has undergone a total reflection on the surface forming the interface of said wall with the second side is avoided by adopting an appropriate form of said interface surface, such that the backscattered light rays which impinge upon said interface surface have an angle of incidence which is less than the angle of total reflection.

According to another feature of the former, the method according to the invention comprises associating a first flat surface forming the interface of said wall with said first side, with a second convex surface forming the interface of said wall with said second side.

According to another feature of the former, said second surface adopts a spherical cap form.

According to an alternative to the preceding feature, said second surface adopts a truncated form.

The invention relates likewise to a device for measuring a light flux backscattered by a dispersed medium located on a first side of a wall, by interaction with a plurality of light rays emitted from the second side of said wall which is opposite the first side, where said dispersed medium is located and in the direction of the latter, said plurality of light rays being able to traverse said wall and being backscattered at least partially by said dispersed medium in the direction of receiving means located on the second side of the wall, said wall being able to be traversed by said emitted and backscattered light rays, and to be in contact with said dispersed medium, said device being characterised in that it comprises:

means for emitting, towards said wall, light radiation which is able to traverse the wall and to reach said dispersed medium, so that the latter can emit in turn, through said wall, a plurality of backscattered light rays with the aim of forming a backscattering spot in which at least one central zone in the form of a disc is defined, the centre of which corresponds to the luminous barycentre of the backscattering spot and the radius of which is equal to four times the maximum free transport length $1^*_{max}$ of said dispersed medium, said backscattering spot being able to be imaged at least in part on said receiving means, means for receiving the light radiation backscattered by said dispersed medium through said wall and intended to form said backscattering spot, said receiving means covering at least one direction extending from the luminous barycentre of said spot, means for suppressing, from light rays backscattered by said dispersed medium, light rays which have emanated from said central zone and have undergone a total reflection on the surface forming the interface of said wall with said second side, means for measuring a spatial sample of the profile of the light flux received by one part at least of said receiving means.

According to another feature, said receiving means extend at least over a surface defined between two said directions which intersect at said luminous barycentre.

According to another feature, the device according to the invention comprises means for calculating the values of the free transport length $1^*$ and the absorption length $1_a$ of said dispersed medium from a measurement of said spatial sample of the profile of the light flux.

According to another feature, said means for suppressing backscattered light rays which have emanated from the central zone and have undergone a total reflection on the surface forming the interface of said wall with said second side, comprise means for diverting, out of said dispersed medium, said light rays which have undergone a total reflection, said diverting means comprising the association of a first surface forming the interface of said wall with said first side, and of a second surface forming the interface of said wall with said second side.

According to another feature of the former, said first and second surfaces are flat and parallel, the usable half-width of said wall, with the aim of forming said backscattering spot, being less than or equal to twice the thickness of said wall minus four times the maximum free transport length $1^*_{max}$ of said dispersed medium.

According to an alternative to the preceding feature, said first surface forming the interface of said wall with said first side is curved, and said second surface forming the interface of said wall with said second side is flat.

According to another feature of the former, said first surface forming the interface of said wall with said first side is cylindrical.

According to another feature, said first surface forming the interface of said wall with said first side is flat, and said second surface forming the interface of said wall with said second side is concave.

According to another feature of the former, said second surface forming the interface of said wall with said second side adopts a conical or truncated form, the axis of the cone or of the truncated part being perpendicular to the first flat surface.

According to another feature, said means for suppressing backscattered light rays which have emanated from said central zone and have undergone a total reflection on the surface forming the interface of said wall with said second side, comprise means for preventing the formation of a said light ray which has undergone a total reflection, on this said surface forming the interface of said wall with the second side.

According to another feature of the former, said means for preventing the formation of a light ray which has emanated from total reflection, on the surface forming the interface of said wall with the second side comprise an appropriate form of said interface surface in order that the backscattered light rays which impinge upon this said interface surface have an angle of incidence which is less than the angle of total reflection.

According to another feature of the former, said means for preventing the formation of a light ray which has emanated from total reflection, on the surface forming the interface of said wall with the second side comprise a first flat surface forming the interface of said wall with said first side associated with a second convex surface forming the interface of said wall with said second side.

According to another feature of the former, said second surface adopts a spherical cap form.

According to an alternative to the preceding feature, said second surface adopts a truncated form.

BRIEF DESCRIPTION OF THE DRAWINGS

The invention will be understood better and other features will appear in the text which follows of examples of the method and device embodiments according to the invention, accompanied by the annexed drawings, examples given by way of illustration and not limiting.

DETAILED DESCRIPTION OF THE INVENTION

Figure 1A:
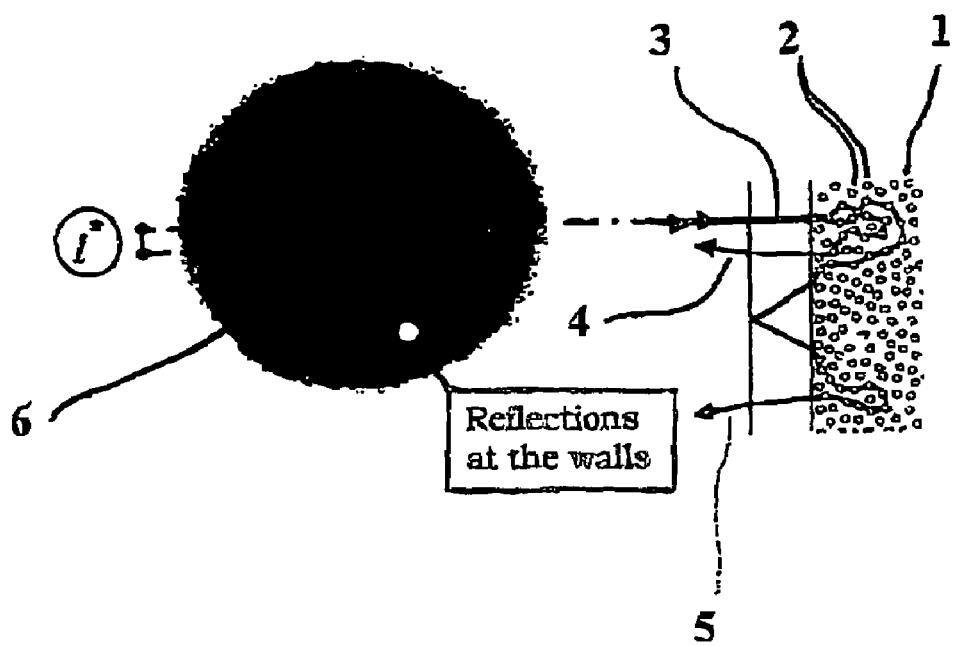
FIG. 1A illustrates the prior art and the problem posed by light rays which have emanated from reflection on the separating wall between the dispersed medium and the means for receiving the light flux.
Figure 1B:
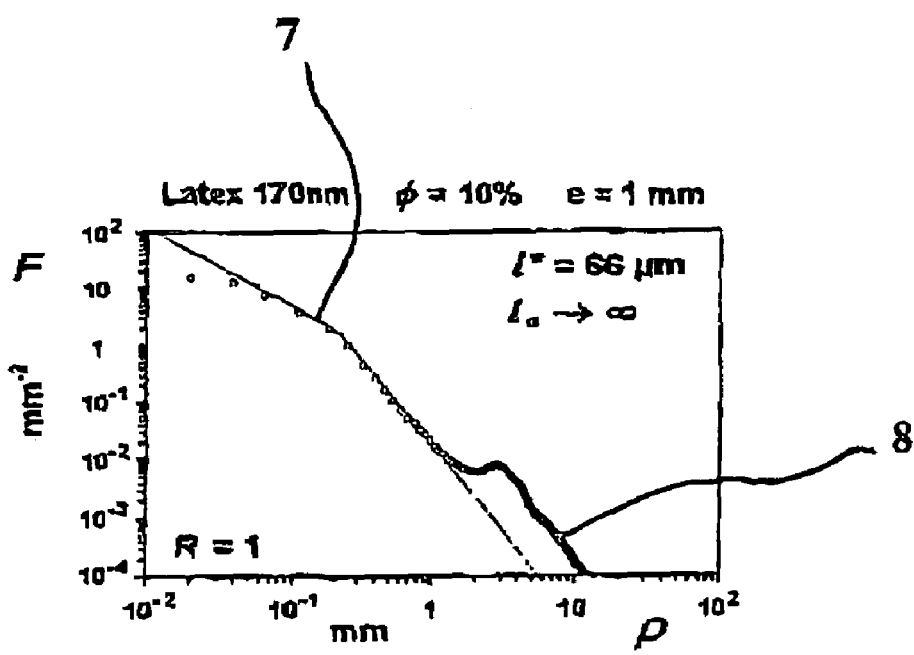
FIG. 1B illustrates the prior art, and more particularly a profile of backscattered light flux comprising light rays which have emanated from reflection on said separating wall, obtained according to the configuration of FIG. 1A.
Figure 3:
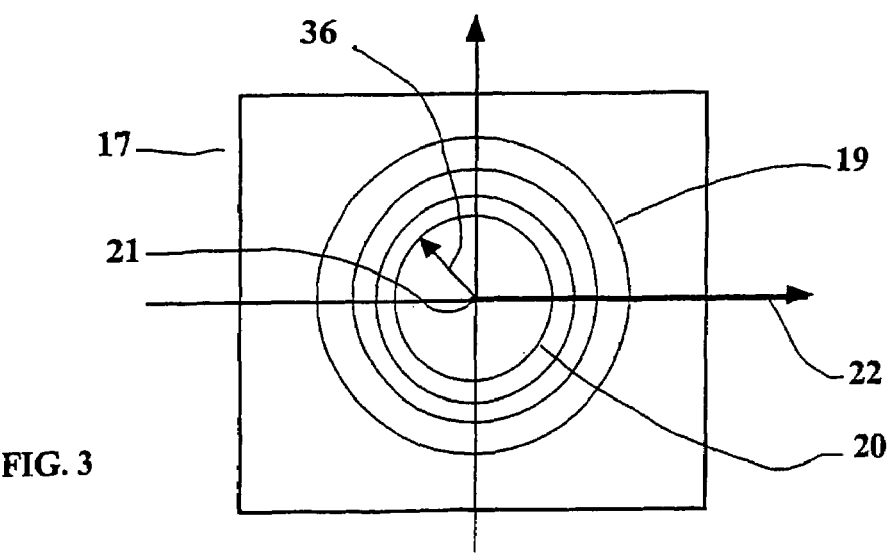
FIG. 3 shows a first detail from the example of FIG. 1.
Figure 4:
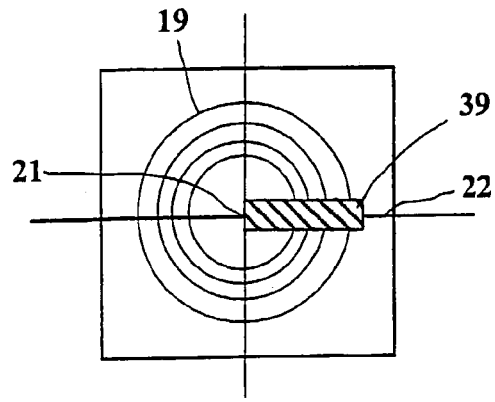
FIG. 4 shows a second detail from the example of FIG. 1.

The device represented in FIGS. 2 to 6 for measuring a light flux 11 backscattered by a dispersed medium 12 located on a first 13 side of a wall 14, by interaction with a plurality of light rays 15 emitted from the second 16 side of this wall 14 which is opposite the first side, where the dispersed medium is located and in the direction of the latter, the plurality of light rays being able to traverse the wall 14 and being backscattered at least partially by the dispersed medium in the direction of receiving means 17 located on the second side of the wall, the wall 14 being able to be traversed by the emitted and backscattered light rays and to be in contact with the dispersed medium, comprises:

means 18 for emitting, towards the wall 14, a light radiation 15 which is able to traverse the latter and to reach the dispersed medium, so that the latter can emit in turn, through the wall 14, a plurality of backscattered light rays 11 with the aim of forming a backscattering spot 19 in which, as represented in FIG. 3, at least one central zone 20 in the form of a disc is defined, the centre 21 of which corresponds to the luminous barycentre of the backscattering spot and the radius 36 of which is equal to four times the maximum free transport length $1^*_{max}$ of the dispersed medium, the backscattering spot 19 being able to be imaged at least in part on the receiving means 17, means 17 for receiving the light radiation backscattered by the dispersed medium through the wall 14 and intended to form the backscattering spot 19, the receiving means covering a direction 22 extending from the luminous barycentre of said spot, as represented in FIG. 4 in the hatched zone, means 23 for suppressing, from light rays backscattered by said dispersed medium, light rays 33 which have emanated from the central zone 20 and have undergone a total reflection on the surface 30 forming the interface of the wall 14 with the second side 16, means 24 for measuring a spatial sample of the profile of the light flux received by one part at least of said receiving means.

The means 18 for emitting light radiation comprise advantageously a monochromatic or polychromatic light source 37, for example a laser diode, with relatively weak or zero angular divergence for preference. The emitted light bundle will be able to be focused in such a manner as to obtain an impact point in the dispersed medium which is as small as possible, at the interface surface 29 between the wall 14 and the dispersed medium. The emitted light bundle will advantageously be substantially perpendicular to the first 29 and second 30 surfaces forming interfaces of the wall 14 with the first 13 and second 16 sides respectively, or substantially perpendicular to surfaces which are tangential to the interface surfaces, when the latter are curved. However, an incident angle of emission up to 25° approximately can be suitable.

The backscattered light flux 11 forms a backscattering spot 19, as described above, which is able to be imaged at least in part thanks to the receiving means 17. The part 39 imaged by the backscattering spot 19 is provided by a light sensor 41, comprising for example a plurality of elementary sensor parts 38, for example a matrix sensor, a CCD camera or a CMOS camera, the arrangement and the extent of the surface which picks up the light representing the part of the backscattering spot which will be imaged, for example on a monitor or in a data set (not represented). In the example represented in FIGS. 2 to 6, the imaged part of the backscattering spot 19 is provided by a plurality of elementary sensor parts 38, or pixels 38, which are aligned according to a direction 22 as defined above. The imaged part of the backscattering spot is therefore formed by a linear band of a width equal to that of a pixel and of an appropriate length, covering for example the totality of the spot following this direction 22 from the centre 21, as represented in FIG. 4 and as will be explained in more detail further on. The receiving means 17 comprise optical means 34 located between the separating wall and the sensor 41, with the aim of moving the image of the backscattering spot over the sensor 41.

The device according to the invention will be provided in order to measure backscattered light fluxes of determined dispersed media, the backscattering spot being a function of the dispersed medium, the determined parameters of which are advantageously to be measured and representative of said medium. There is determined, with the aim of constructing the device, the maximum value of the free transport length 1* of the dispersed medium which it will be possible to measure if necessary, i.e. $1^*_{max}$, in order to determine the maximum extent of the backscattering spot which will be able to be imaged with enlargement adapted according to any known means, and therefore the extent of the sensor 41 which will be recommended, as will be explained further on, with the description of a model for defining the connection between the flux of measured backscattered light and the calculation of the values of the free transport length 1* and of the absorption length $1_a$ of the dispersed medium 12.

Figure 2:
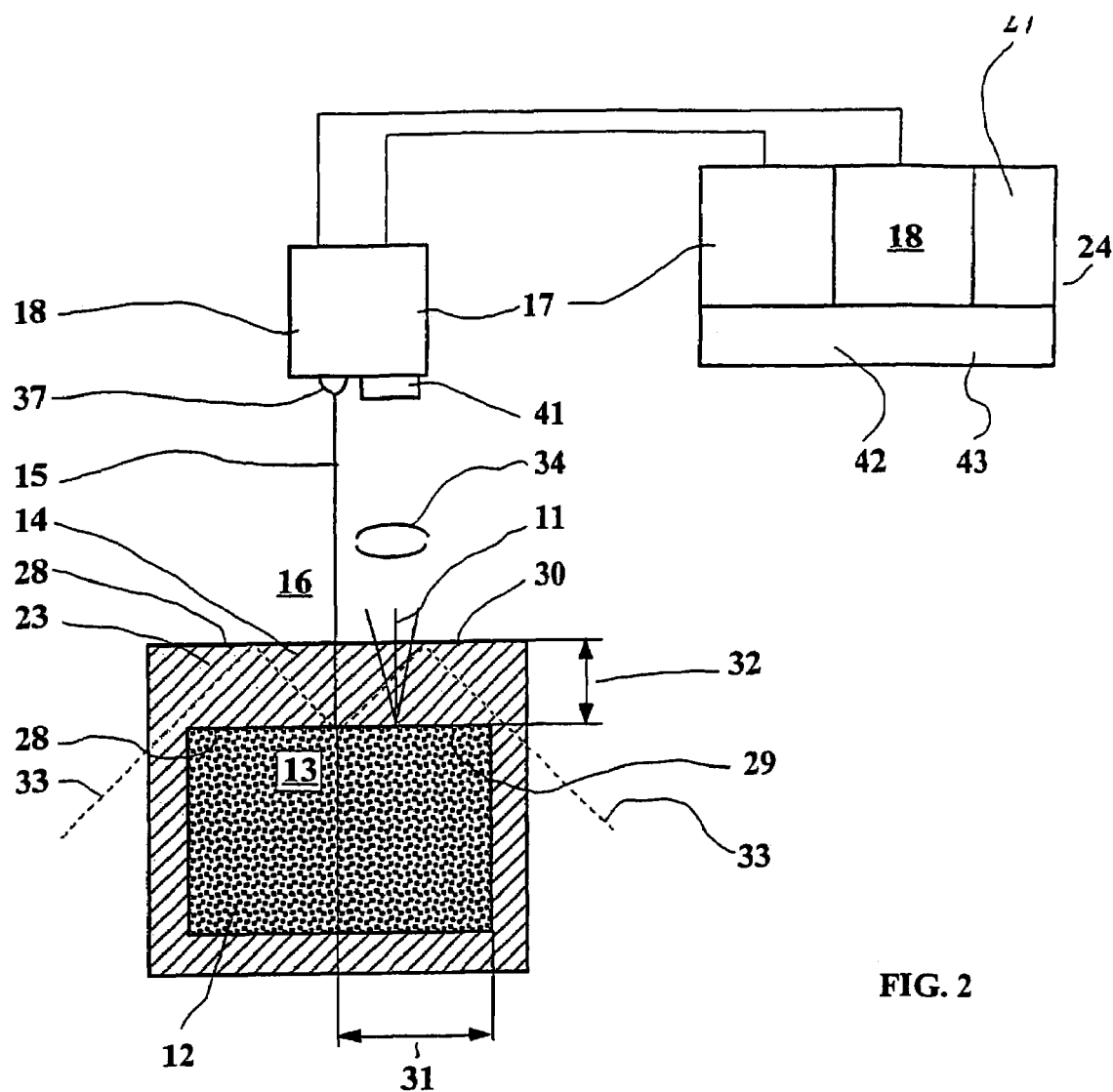
FIG. 2 shows a schematic plan view of a first embodiment of a device according to the invention for measuring a light flux backscattered by a dispersed medium.

The means 23 for suppressing, from light rays backscattered by the dispersed medium 12, light rays 33 which have emanated from the central zone 20 and have undergone a total reflection on the surface 30 forming the interface of the wall 14 with the second side 16, comprise means 28 for diverting, out of the dispersed medium 12, light rays which have emanated from total reflections, the means for diverting, out of the dispersed medium, light rays which have emanated from total reflections comprising the association of the first 29 surface forming the interface of the wall 14 with the first 13 side and of the second 30 surface forming the interface of the wall 14 with the second 16 side. In the example of FIG. 2, the first 29 and second 30 surfaces are flat and parallel, the usable half-width 31 of the wall 14, with the aim of forming the backscattering spot 19, being less than or equal to twice the thickness 32 of the wall 14 minus four times the maximum free transport length $1^*_{max}$ of the dispersed medium 12. One must have:

$r_{max}=2ep-41^*_{max}$, with $r_{max}$=radius of the usable field of vision, identified in the example by the half-width of the wall 14, as represented in FIG. 2, ep=thickness 32 of the wall 14, at the position where the emitted light radiation traverses this wall, as represented in FIG. 2, $1^*_{max}$=maximum free transport length of the dispersed medium studied in the device.

In FIG. 2 there are represented two examples of light rays 33 backscattered by the medium 12 from the point of contact of the emitted radiation, then reflected on the surface 30 according to an angle of total reflection, and which are diverted out of the dispersed medium 12.

The means 24 for measuring a spatial sample of the profile of the light flux received by one part at least of the receiving means 17, comprise a computer 42 which is able to calculate the profile of the light flux received by one part at least of the sensor 41, determined according to requirements, or the totality of the light flux received by the sensor 41. The measurement means 24 comprise furthermore control means 43 for selecting the part of the sensor 41 for which the light flux backscattered by the dispersed medium 12 is to be calculated, if necessary.

The measurement means 24 comprise furthermore advantageously means 27 for calculating the values of the free transport length 1* and the absorption length $1_a$ of the dispersed medium 12 from a measurement of the spatial sample of the profile of the light flux. In order to allow calculation of the values 1* and $1_a$, the device will use advantageously a calculation model which will be incorporated in the calculation means 27, comprising two distinct theorems according to the zone of the measured backscattered flux:

from the luminous barycentre of the backscattering spot and up to a distance r extending up to a value equal to 4 1* of the luminous barycentre, i.e. for r belonging to the interval [0, 4 1*], termed zone of short photons, the applicable theorem will advantageously be the following:

$$F(r) = \frac{1}{\pi 4^{1.6}} 1^{*-0.6} r^{-1.4} e\left(-1.3 \frac{r}{(1^* 1_a)^{1/2}}\right)$$

the theorem in which the factor e=2.71828, π=3.14159, F(r)=the illumination (surface energy) at the distance r from the centre of the spot. From a measurement of the flux F(r), the calculation means 27 therefore determine the values of 1* and $1_a$ relative to the dispersed medium.

from the distance r=4 1* and up to the end of the spot, i.e. for r belonging to the interval [4 1*, ∞], termed zone of long photons, in practice up to the end of the sensor 41 the furthest away from the luminous barycentre of the spot, the applicable theorem will be the following:

$$F(r) = \frac{1^*}{\pi r^3} e\left(-1.3 \frac{r}{(1^* 1_a)^{1/2}}\right)$$

the theorem in which the factor e=2.71828, π=3.14159, F(r)=the illumination (surface energy) at the distance r from the centre of the spot. From a measurement of the flux F(r), the calculation means 27 determine therefore the values of 1* and of $1_a$ relative to the dispersed medium.

It should be noted that the above model supposes an infinite illumination at the centre of the spot; this emanates from the supposed punctiform injection of the light radiation emitted in this case. According to this model, the emitted light radiation 15 will therefore be as concentrated as possible at the point of impact in the dispersed medium 12, as indicated above.

Figure 7:
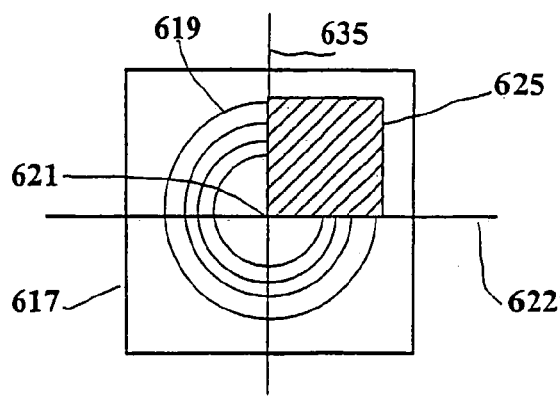
FIG. 7 shows a second example of the second detail of FIG. 4.
Figures 5, 8:
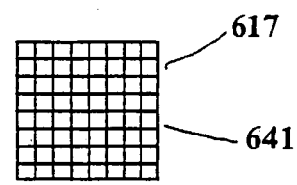
FIG. 5 shows a third detail from the example of FIG. 1, in front view.
FIG. 8 shows a detail from the second example of FIG. 7, in front view.
Figures 6, 9:
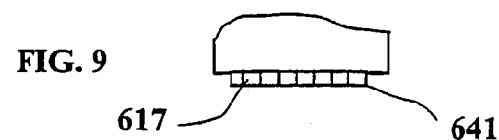
FIG. 6 shows the detail according to FIG. 5, in plan view.
FIG. 9 shows the detail of the second example of FIG. 7, in plan view.

FIGS. 7 to 9 show another example of receiving means 617, in which the elements similar to those of the preceding example bear the same references with the addition of the number 600. The sensor 641 comprises a plurality of elementary sensor parts 638, for example a matrix sensor, a CCD camera or a CMOS camera, extending over a surface 625 defined between two directions 622, 635 which intersect at the luminous barycentre 621, as represented in FIG. 7. As represented in FIGS. 8 and 9, the sensor 641 adopts a substantially square shape in order to ensure the reception of a quarter of the backscattering spot. It should be noted that, alternatively, the sensor can adopt a circular sector shape (not represented) in order to "stick" as close as possible to the exterior perimeter of the spot 619.

Figure 10:
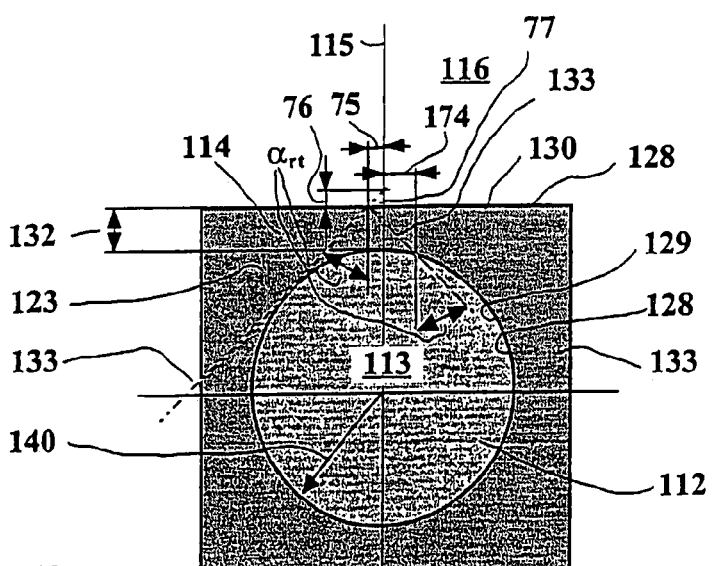
FIG. 10 shows a partial schematic plan view of a second embodiment of a device according to the invention for measuring a light flux backscattered by a dispersed medium.

FIG. 10 illustrates a second example of the separating wall 114 between the dispersed medium 112 and the receiver of the light flux. In FIG. 10, the elements similar to those of the example illustrated in FIGS. 2 to 6 bear the same references with the addition of the number 100. In the example of FIG. 10, the means 123 for suppressing backscattered light rays which have emanated from the central zone and have undergone a total reflection on the surface 130 forming the interface of the wall 114 with the second side 116, comprise means 128 for diverting, out of the dispersed medium 112, light rays which have emanated from total reflections, the means for diverting, out of the dispersed medium, light rays which have emanated from total reflections comprising the association of a first 129 surface forming the interface of the wall 114 with the first 113 side, and of a second 130 surface forming the interface of the wall 114 with the second 116 side, the first surface 129 forming the interface of the wall 114 with the first 113 side being curved, and the second 130 surface forming the interface of the wall with the second 116 side being flat.

According to the device of FIG. 10, the first surface 129 forming the interface of the wall 114 with the first 113 side is advantageously cylindrical, and has a radius 140 determined for example by the following calculation; given that:

$\alpha_{rt}$=Brewster or limit incidence angle before total reflection=arcsin(l/n)

$n_p$=optical index of the material forming the wall 114, ep=thickness 132 of the wall 114, according to the axis 115 corresponding to a diameter of the cylindrical surface with a circular section 120, at the position where the emitted light radiation traverses this wall, it is noted:

e'=distance 76 between the surface 130 forming the interface of the wall 114 with the second side 116 and an intersection point between the axis 115 and the oblique emergent ray 77, d=distance 75 between the axis 115 and the point of impact of the oblique emergent ray 77.

It is sought to determine $r_i$=radius of the cylinder with a circular section forming the first surface 129: there are the following equations, knowing that the reflected ray 133 is a tangent to the surface 129:

$\sin(\alpha_{rt}) = r_i/(r_i + ep + e')$ $d = ep \tan(\alpha_{rt}) - 4l^*$ $e' = d/\tan(\alpha_{rt})$ one can therefore calculate $r_i = (2ep - 4l^*_{max}/\tan(\alpha_{rt}))l/(n_p - 1)$.

An example of a light ray which has undergone a total reflection on the surface 130 and which is diverted out of the dispersed medium 112 is represented with the reference 133 in FIG. 10. It should be noted that the backscattered ray 133 represented in FIG. 10 is offset by a distance 174 equal to 4 $1^*_{max}$, i.e. it is included in the light rays which have emanated from said central zone and have undergone a total reflection on the interface surface 130. It should be noted that in the particular case where the width of the spot is not taken into account, i.e. if one considers $1^*_{max}=0$, there is obtained:

$r_i = 2ep/(n_p - 1)$

A numerical application of the preceding example gives: for a wall 114 made of glass, np=1.5, 1*max=0.5 mm, ep=5 mm, one obtains ri=15.5 mm.

Figure 11:
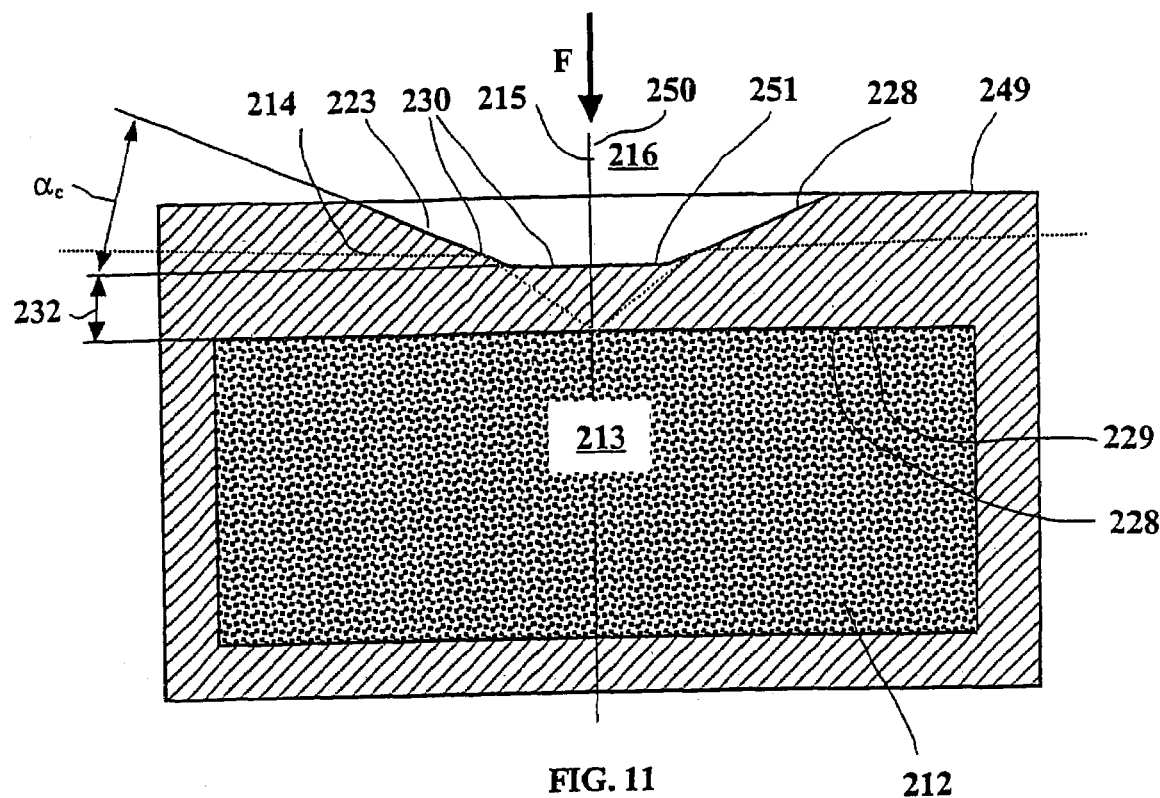
FIG. 11 shows a partial schematic plan view of a third embodiment of a device according to the invention for measuring a light flux backscattered by a dispersed medium.
Figure 12:
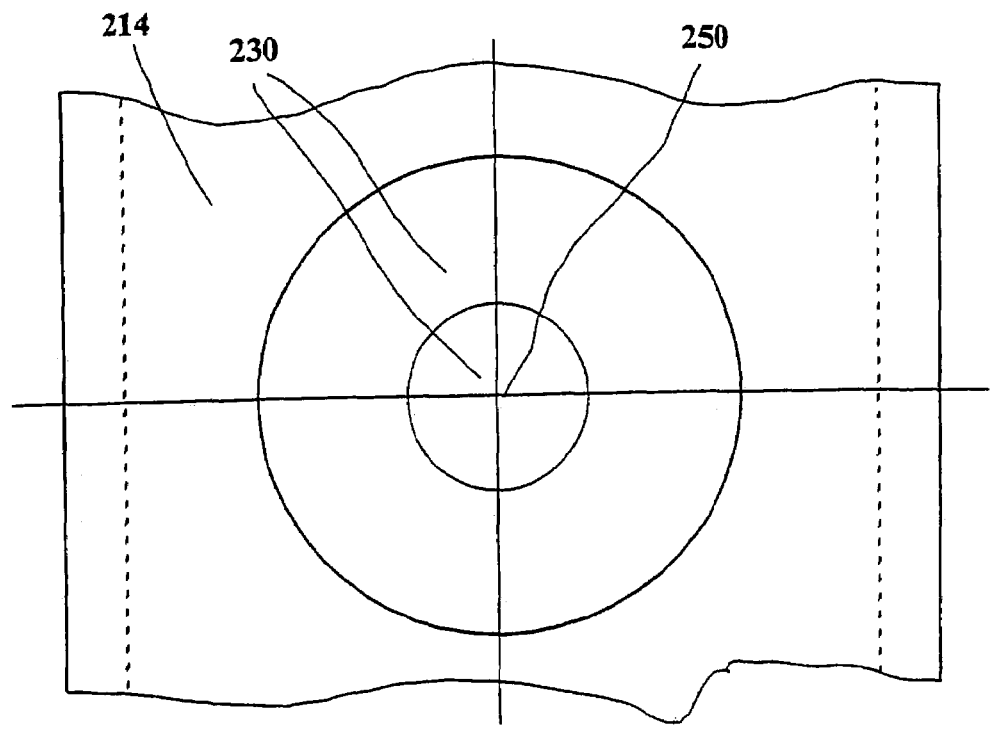
FIG. 12 shows a partial schematic front view of the third example according to FIG. 11.

FIGS. 11 and 12 illustrate a third example of the separating wall 214 between the dispersed medium 212 and the receiver of the light flux. In FIGS. 11 and 12, the elements similar to those of the example illustrated in FIGS. 2 to 6 bear the same references with the addition of the number 200. In the example of FIGS. 11 and 12, the means 223 for suppressing the backscattered light rays which have emanated from the central zone and have undergone a total reflection on the surface 230 forming the interface of the wall 214 with the second 216 side, comprise means 228 for diverting, out of the dispersed medium 212, light rays which have emanated from total reflections, the means for diverting, out of the dispersed medium, light rays which have emanated from total reflections comprising the association of a first 229 surface forming the interface of the wall 214 with the first 213 side, and of a second 230 surface forming the interface of the wall 214 with the second 216 side, the first 229 surface forming the interface of the wall 214 with the first 213 side being flat, and the second 230 surface forming the interface of the wall with the second 216 side being concave.

According to the device of FIGS. 11 and 12, the second 230 surface forming the interface of the wall 214 with the second 216 side adopts a conical form (not represented) or truncated as represented in FIG. 11, the axis 250 of the cone (not represented) or of the truncated part being perpendicular to the first 229 flat surface. The truncated part will be determined so that the rays reflected by the medium having too great an incidence and which therefore would have to be reflected totally meet the conical part and will thus be cast towards the edges, out of the medium 212, as represented in FIG. 11. The rays having a yet higher incidence meet a flat surface 249 adjacent to and surrounding the truncated part which will suffice to cast them to the outside of the dispersed medium 212.

The angle $\alpha_c$ of the truncated part, as represented in FIG. 11, will be substantially equal to:

$\pi/2 - (\pi/2 - \alpha_{rt})/2 + \text{atan}(ep/r_{max})$ with:

$\alpha_{rt}$=Brewster or limit incidence angle before total reflection=arcsin(l/n)

ep=thickness 232 of the wall 214 at the place where the emitted light radiation traverses this wall, i.e. between the surfaces 251 and 229, as represented in FIG. 2, $r_{max}$=radius of the usable field of vision determined according to requirements.

The flat circular zone 251 forming the top of the truncated part will have a radius $r_s$ determined by the following formula:

$$r_s = (ep \tan(\alpha_{rt})) - 41^*_{max}$$

and the large base of the truncated part will have a minimum radius $r_b$ at least equal to $r_{max}/2$. The approximate thickness of the wall 214 between the flat surfaces 229 and 249 is given according to the following formula:

$$ep + r_{max}/2(\pi/2 - \alpha_{rt})/2$$

A numerical application comprises taking a material of optical index $n_p=1.5$ for the separating wall, a radius of the usable field of vision $r_{max}=20$ mm, and a maximum free transport length $1^*_{max}=0.5$ mm, this gives for each of the examples above, FIGS. 2, 10 and 11:

wall 14 plane-plane (FIG. 2): ep=11 mm, wall 114 plane-cylinder: $r_i=40$ mm, ep=20 mm, wall 214 cone-plane: $\alpha_{rt}=41.8$ degrees, $r_s=1$ mm, $\alpha_c=20$ degrees approximately, ep=3.5 mm, thickness of the wall 214 between the flat surfaces 229 and 249=3.5+3.5=7 mm.

Figure 13:
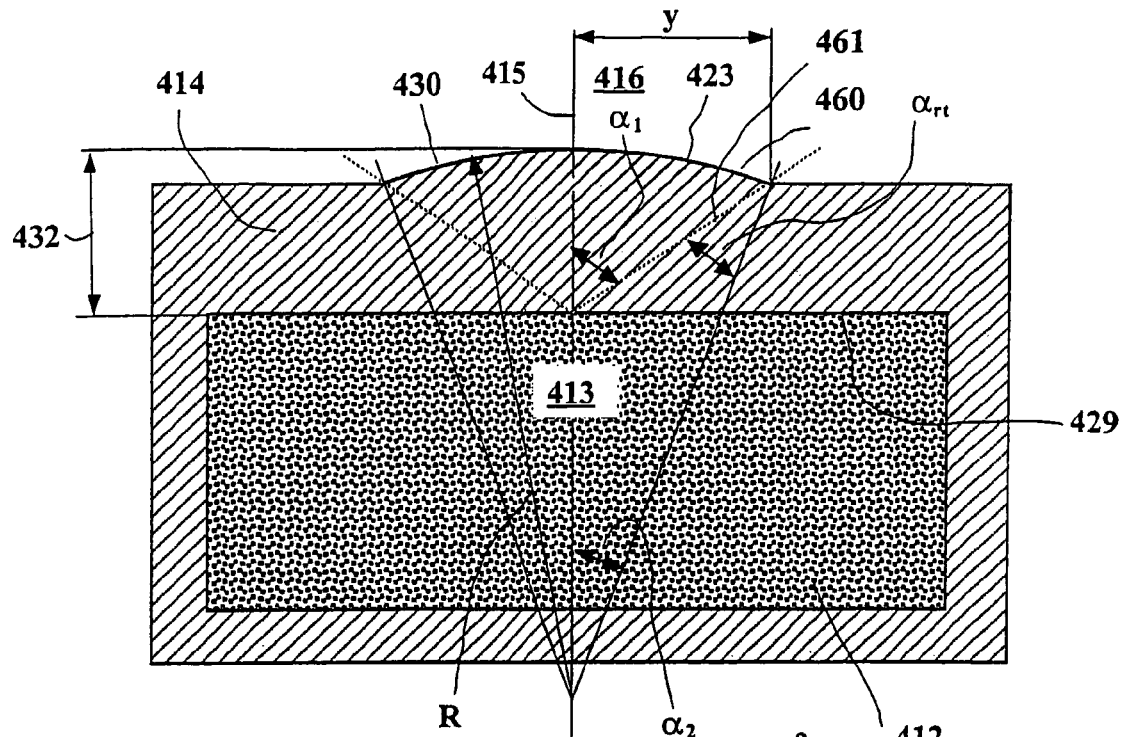
FIG. 13 shows a partial schematic plan view of a fourth embodiment of a device according to the invention for measuring a light flux backscattered by a dispersed medium.

In the fourth example described by means of FIG. 13, the elements similar to those of the example illustrated in FIGS. 2 to 6 bear the same references with the addition of the number 400. The means 423 for suppressing backscattered light rays which have emanated from total reflection on this surface forming the interface of the wall 414 with the second 416 side, comprise means 460 for preventing the formation of a light ray which has emanated from the central zone and has undergone a total reflection on the surface 430 forming the interface of the wall 414 with the second 416 side. Hence, contrary to the preceding examples, the aimed reflected rays are no longer diverted out of the dispersed medium of concern, but their generation is prevented. In fact, the means 460 for preventing the formation of a light ray which has emanated from the central zone and is able to undergo a total reflection on the surface 430 forming the interface of the wall 414 with the second 416 side, comprise an appropriate form of the interface surface 430 in order that the backscattered light rays which impinge upon this interface surface 430 have an angle of incidence less than the angle of total reflection.

According to the example of FIG. 13, the means 460 for preventing the formation of a light ray which emanates from total reflection on the surface 430 forming the interface of the wall 414 with the second 416 side comprise a first 429 flat surface forming the interface of the wall 414 with the first 413 side associated with a second 430 convex surface, in the example according to FIG. 13 a second surface adopting the form of a spherical cap forming the interface of the wall 414 with the second side 416.

In order to form the spherical cap, it is possible to use a blade with flat parallel faces, on which a plano-convex lens is glued. This therefore concerns an assembly of standard optical components. Furthermore, the effect of this form on the imagery of the camera is easily foreseeable. The approximate calculation according to the theorems of trigonometry provides the following equations:

$$\sin(\alpha_2) = y/R \quad \text{(equation 1)}$$

$$\tan(\alpha_1) = y/(ep - R(1 - \cos(\alpha_2))) \quad \text{(equation 2)}$$

the condition for an extreme backscattered ray 461, which exits for example at the referenced distance y from the centre of FIG. 13, to undergo a refraction and not a reflection, is that:

$$\alpha_1 - \alpha_2 = \alpha_{rt} \quad \text{(equation 3)}$$

a relation has thus been defined between the parameters ep 432, R and y. Given that the optical index $n_s$ of the dispersed medium 413 is less than the optical index $n_p$ of the material of the wall 414, the incidence of the emergent rays will be limited to $\alpha_{1max}$, such that:

$$n_p \sin(\alpha_{1max}) = n_s \text{ with}$$

$n_p$=optical index of the material of the wall 414, $n_s$=optical index of the dispersed medium 413, $\alpha_2$ is therefore deduced thanks to equation 3. In order to use these equations, one begins by proposing a value of R. Then the value y is deduced thanks to equation 1, and finally the value ep of the wall according to the axis 415, thanks to equation 2. The thickness of the lens to be glued on is determined and the base or thickness of the blade with flat parallel faces are determined from the values derived from the preceding calculation and affined by radius lines. A numerical application of the example according to FIG. 13 is given below.

For a wall made of glass and water as the dispersed medium, there is $\alpha_{1max}=62.45$ degrees; one can choose for example R=30 mm; therefore y=10.58 mm. The thickness ep of the wall at the centre according to the axis 415 is 6.52 mm. The thickness at the centre according to the axis 415 of the lens to be glued on is 1.93 mm, and the blade with flat faces has a thickness of 4.59 mm.

Figure 14:
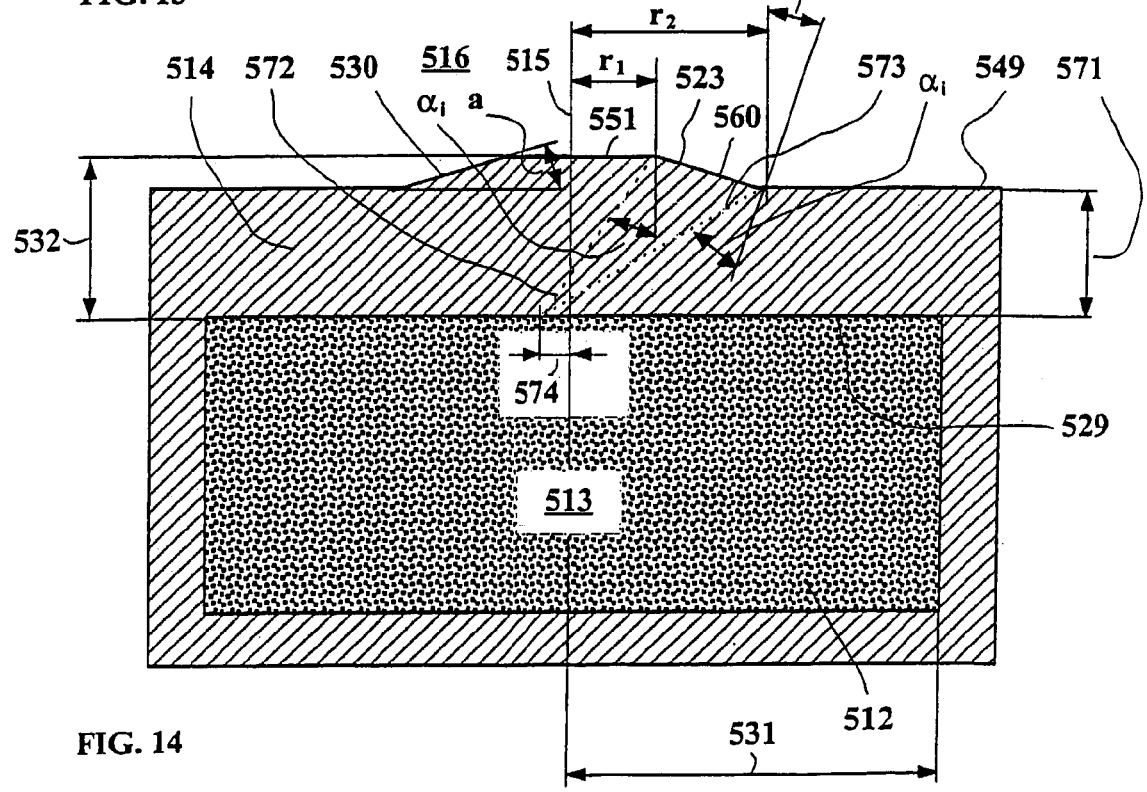
FIG. 14 shows a partial schematic plan view of a fifth embodiment of a device according to the invention for measuring a light flux backscattered by a dispersed medium.

In the fifth example described by means of FIG. 14, the elements similar to those of the example illustrated in FIGS. 2 to 6 bear the same references with the addition of the number 500. The example according to FIG. 14 is analogous to the example according to FIG. 13, with the exception of the second 530 surface adopting a truncated form, which is calculated however according to considerations similar to those of the example according to FIG. 13. In the example described by means of FIG. 14, the means 523 for suppressing backscattered light rays which have emanated from total reflection on the surface forming the interface of the wall 514 with the second 516 side, comprise means 560 for preventing the formation of a light ray which has emanated from the central zone and has undergone a total reflection on this surface 530 forming the interface of the wall 514 with the second 516 side. The means 560 for preventing the formation of a light ray which has emanated from the central zone and has undergone a total reflection on the surface 530 forming the interface of the wall 514 with the second 516 side comprise an appropriate form of the interface surface 530 in order that backscattered light rays which have emanated from said central zone, for example the extreme light rays 572, 573 which impinge upon this interface surface 530, have an angle of incidence $\alpha_t$ which is less than the angle of total reflection. The second 530 surface adopts a truncated form.

The parameters of the truncated interface 530 are for example determined in the following manner. There are set:

$\alpha_{rt}$=Brewster or limit incidence angle before total reflection, a=angle which defines the truncated part, as represented in FIG. 14, $r_1$=radius of the top (small base 551) of the truncated part, $r_2$=radius of the base (large base) of the truncated part, ep=thickness 532 of the wall 514 according to the axis 515, $e_{ext}$=thickness 571 of the wall 514 between the interface surfaces 529 and 549, $r_{max}$=radius of the usable field of vision, identified in the example as the half-width of the wall 514, as represented in FIG. 14;

the limit backscattered light ray 573 again exiting via the truncated part must have an incidence $\alpha_i$ equal to the Brewster angle $\alpha_{rt}$: this gives:

$$\text{Tan}(a+\alpha_{rt})=(41*_{max}+r_2)/e_{ext} \quad \text{(equation 4)}$$

the limit backscattered light ray 573 is represented offset from the axis 515 by a distance 574 corresponding to 4 $1*_{max}$. Remember that: $1*_{max}$=maximum free transport length of the dispersed medium studied in the device. A limit backscattered light ray 572 again exiting via the small base 551 of the truncated part must have an incidence $\alpha_i$ equal to the Brewster angle $\alpha_{rt}$: this gives:

$$\text{Tan}(\alpha_{rt})=(41*_{max})+r_1)/ep \quad \text{(equation 5)}$$

the truncated part which connects the small base 551 of radius $r_1$ to the large base of radius $r_2$ and given by the angle a is provided with the following formula:

$$\text{Tan}(a)=(ep-e_{ext})/(r_2-r_1) \quad \text{(equation 6)}$$

the backscattered light ray reflected by the flat surface 549, adjacent to and surrounding the truncated part, undergoes a total reflection but will exit via the edge of the vessel without returning into the medium 512: this gives:

$$41*_{max}+r_2=r_{max}/2 \quad \text{(equation 7)}$$

In order to calculate a vessel intended to receive the diffuse medium 513, $r_2$ is determined from equation 7, a is calculated from equation 4, then ep is calculated from equations 5 and 6: this gives:

$$ep=(e_{ext}+\text{Tan}(a)(41*_{max}+r_2))/(1/\text{Tan}(a)\text{Tan}(\alpha_{rt})) \quad \text{(equation 8)}$$

then $r_1$ is calculated from equation 5. A numerical application example is the following: there is given $e_{ext}$=5 mm, $r_{max}$=20 mm; thus from equation 7, $r_2$=10 mm is obtained, then from equation 4, a=21.6° is obtained, then from equation 8, ep=6.61 mm is obtained, and finally from equation 5, $r_1$=3.91 mm is obtained.

It should be noted that the separating walls 14, 14, 214, 414, 514 can each be included in a vessel intended to contain the dispersed medium, of which the backscattered flux is to be measured, or to form the wall of a probe, which separates the receiver of the backscattered light flux and the dispersed medium, the wall of the probe being therefore brought in contact with the dispersed medium.

It should likewise be noted that models other than the one which has been described here can be used to exploit the devices according to the invention, in particular those described above.

Several method examples according to the invention will now be described. By means of FIGS. 2 to 6, 10, 11, 12, the method allows measurement of a backscattered light flux 11, 111, 211, by a dispersed medium 12, 112, 212, for example an emulsion, a suspension, a polyphase medium, or similar, located on a first 13, 113, 213 side of a wall 14, 114, 214, by interaction with a plurality of light rays 15, 115, 215, emitted from the second 16, 116, 216 side of the wall 14, 114, 214 which is opposite the first side, where the dispersed medium is located and in the direction of the latter, the plurality of light rays being able to traverse the wall and being backscattered at least partially by the dispersed medium in the direction of receiving means 17 located on the second side of the wall, the method comprising at least the following steps:

emitting the plurality of light rays 15, 115, 215, in the direction of said dispersed medium and through the wall 14, 114, 214, so that said dispersed medium is able to emit in turn, through the wall, a plurality of backscattered light rays 11, 111, 211 with the aim of forming a backscattering spot 19 in which at least one central zone 20 in the form of a disc is defined, the centre 21 of which corresponds to the luminous barycentre of the backscattering spot 20 and the radius 36 of which is equal to four times the maximum free transport length $1*_{max}$ of the dispersed medium, the backscattering spot 19 being able to be imaged at least in part on the receiving means 17, forming the backscattering spot 19 from backscattered light rays which have traversed the wall and are free, according to a direction 22 extending from the luminous barycentre of the backscattering spot, of light rays which have emanated from the central zone 20 and have undergone a total reflection on the surface 30, 130, 230, forming the interface of the wall 14, 114, 214 with the second 16, 116, 216 side, avoiding the return into the dispersed medium of light rays which have emanated from this central zone 20 and have undergone a total reflection on the surface 30, 130, 230, measuring a spatial sample of the profile of the light flux in the thus obtained backscattering spot 19, extending in the direction 22, determining the values of the free transport length $1*$ and of the absorption length $1_a$ using a determined photon-dispersion interaction model, from the spatial sample of the profile of the light flux, for example the model described above.

According to another example of the method according to the invention, described by means of FIGS. 7 and 9, it comprises repeating the steps described above with the exception of the steps comprising forming the backscattering spot and measuring a spatial sample of the profile of the light flux, replaced by the following:

forming said backscattering spot 619 from backscattered light rays which have traversed the wall 14, 114, 214, and are free, between two directions 622, 635 extending from the luminous barycentre of the spot, of light rays which have emanated from the central zone and have undergone a total reflection on the surface 30, 130, 230, forming the interface of the wall with the second side 16, 116, 216, avoiding the return into the dispersed medium of light rays which have emanated from this central zone 20 and have undergone a total reflection on the surface 30, 130, 230.

measuring at least one spatial sample of a profile of the light flux in said thus obtained backscattering spot 619, extending at least over a surface 625 defined between the two directions 622, 635 which intersect at the luminous barycentre.

Alternatively, another example of the method according to the invention is described below by means of FIG. 13 or 14. It comprises avoiding the total reflection of a light ray which has emanated from the central zone and has undergone a total reflection on the surface forming the interface of said wall 414, 514 with the second 416, 516 side, through which the backscattered light rays pass which are intended to form the backscattering spot, by adopting an appropriate form of the interface surface 430, 530 such that the backscattered light rays which impinge upon this interface surface have an angle of incidence less than the angle of total reflection. The method comprises advantageously associating a first 429, 529 flat surface forming the interface of the wall 414, 514 with the first 413, 513 side, with a second 430, 530 convex surface forming the interface of the wall with the second 416, 516 side.

The invention claimed is:

1. Method for measuring a light flux backscattered by a dispersed medium located on a first side of a wall, by interaction with a plurality of light rays emitted from the second side of said wall which is opposite the first wall, said plurality of light rays being able to traverse said wall and being backscattered at least partially by said dispersed medium in the direction of receiving means located on the second side of the wall, wherein said method comprises at least the following steps:

emitting said plurality of light rays in the direction of said dispersed medium and through said wall so that said dispersed medium is able to emit in turn, through said wall, a plurality of backscattered light rays with the aim of forming a backscattering spot in which at least one central zone in the form of a disc is defined, the centre of which corresponds to the luminous barycentre of the backscattering spot and the radius of which is equal to four times the maximum free transport length ($1^*_{max}$) of said dispersed medium, said backscattering spot being able to be imaged at least in part on said receiving means, forming said backscattering spot from backscattered light rays which have traversed said wall and, at least according to a direction extending from the luminous barycentre of said backscattering spot, are free of light rays which have emanated from said central zone and have undergone a total reflection on the surface forming the interface of said wall with said second side, measuring at least one spatial sample of a profile of the light flux in said backscattering spot, extending in said at least one direction, and recording the measurement of the light flux thus measured.

2. Method according to claim 1, wherein it comprises:

forming said backscattering spot from backscattered light rays which have traversed said wall and, between two directions extending from the luminous barycentre of said spot, are free of light rays which have emanated from said central zone and have undergone a total reflection on the surface forming the interface of said wall with said second side, measuring at least one spatial sample of a profile of the light flux in said thus obtained backscattering spot, extending at least over a surface defined between the two said directions which intersect at said luminous barycentre.

3. Method according to claim 1, which comprises furthermore determining the values of the free transport length ($1^*$) and of the absorption length ($1_a$) using a determined photon-dispersion interaction model, from said spatial sample of a profile of the light flux.

4. Method according to claim 1, which further comprises avoiding the return into said dispersed medium of the light rays which have emanated from said central zone and have undergone a total reflection on the surface forming the interface of said wall with the second side.

5. Method according to claim 4, which further comprises associating a first surface forming the interface of said wall with said first side, with a second surface forming the interface of said wall with said second side, said first and second surfaces being parallel.

6. Method according to claim 5, wherein the usable half-width of said wall is less than or equal to twice the thickness of said wall minus four times the maximum free transport length ($1^*_{max}$) of said dispersed medium.

7. Method according to claim 4, which further comprises associating a first surface forming the interface of said wall with said first side, with a second surface forming the interface of said wall with said second side, said first and second surfaces being non-parallel.

8. Method according to claim 7, wherein said first surface forming the interface of said wall with said first side is curved, and said second surface forming the interface of said wall with said second side is flat.

9. Method according to claim 8, wherein said first surface forming the interface of said wall with said first side is cylindrical.

10. Method according to claim 7, wherein said first surface forming the interface of said wall with said first side is flat, and said second surface forming the interface of said wall with said second side is concave.

11. Method according to claim 10, wherein said second surface forming the interface of said wall with said second side is conical or truncated.

12. Method according to claim 1, which further comprises avoiding the total reflection of a light ray which has emanated from said central zone and has undergone a total reflection on the surface forming the interface of said wall with the second side, though which the backscattered light rays pass which are intended to form said backscattering spot.

13. Method according to claim 12, wherein the formation of a light ray which has emanated from said central zone and has undergone a total reflection on the surface forming the interface of said wall with the second side is avoided by adopting an appropriate form of said interface surface such that the backscattered light rays which impinge upon said interface surface have an angle of incidence ($\alpha_t$) which is less than the angle of total reflection.

14. Method according to claim 13, which further comprises associating a first flat surface forming the interface of said wall with said first side, with a second convex surface forming the interface of said wall with said second side.

15. Method according to claim 14, wherein said second surface adopts a spherical cap form.

16. Method according to claim 14, wherein said second surface adopts a truncated form.

17. Device for measuring a light flux backscattered by a dispersed medium located on a first side of a wall, by interaction with a plurality of light rays emitted from the second side of said wall which is opposite the first side, said plurality of light rays being able to traverse said wall and being backscattered at least partially by said dispersed medium in the direction of receiving means located on the second side of the wall, said wall being able to be traversed by said emitted and backscattered light rays, and to be in contact with said dispersed medium, wherein said device comprises:

means for emitting, towards said wall, a light radiation which is able to traverse the wall and to reach said dispersed medium, so that the latter can emit in turn, through said wall, a plurality of backscattered light rays with the aim of forming a backscattering spot in which at least one central zone in the form of a disc is defined, the centre of which corresponds to the luminous barycentre of the backscattering spot and the radius of which is equal to four times the maximum free transport length ($1^*_{max}$) of said dispersed medium, said backscattering spot being able to be imaged at least in part on said receiving means, means for receiving light radiation backscattered by said dispersed medium through said wall and intended to form said backscattering spot, said receiving means covering at least one direction extending from the luminous barycentre of said spot, means for suppressing, from light rays backscattered by said dispersed medium, light rays which have emanated from said central zone and have undergone a total reflection on the surface forming the interface of said wall with said second side, means for measuring a spatial sample of the profile of the light flux received by one part at least of said receiving means.

18. Device according to claim 17, which further comprises means for calculating the values of the free transport length ($1^*$) and the absorption length ($1_a$) of said dispersed medium from a measurement of said spatial sample of the profile of the light flux.

19. Device according to claim 17, wherein said means for suppressing backscattered light rays which have emanated from said central zone and have undergone a total reflection on the surface forming the interface of said wall with said second side, comprise means for diverting, out of said dispersed medium, said light rays which have undergone a total reflection, said diverting means comprising the association of a first surface forming the interface of said wall with said first side, and of a second surface forming the interface of said wall with said second side.

20. Device according to claim 19, wherein said first and second surfaces are flat and parallel, the usable half-width of said wall, with the aim of forming said backscattering spot, being less than or equal to twice the thickness of said wall minus four times the maximum free transport length ($1^*_{max}$) of said dispersed medium.

21. Device according to claim 19, wherein said first surface forming the interface of said wall with said first side is curved, and said second surface forming the interface of said wall with said second side is flat.

22. Device according to claim 21, wherein said first surface forming the interface of said wall with said first side is cylindrical.

23. Device according to claim 19, wherein said first surface forming the interface of said wall with said first side is flat, and said second surface forming the interface of said wall with said second side is concave.

24. Device according to claim 23, wherein said second surface forming the interface of said wall with said second side adopts a conical or truncated form, the axis of the cone or of the truncated part being perpendicular to the first flat surface.

25. Device according to claim 17, wherein said means for suppressing backscattered light rays which have emanated from said central zone and have undergone a total reflection on the surface forming the interface of said wall with said second side, comprise means for preventing the formation of a said light ray which has undergone a total reflection, on this said surface forming the interface of said wall with the second side.

26. Device according to claim 25, wherein said means for preventing the formation of a light ray which has emanated from total reflection, on the surface forming the interface of said wall with the second side comprise an appropriate form of said interface surface in order that the backscattered light rays which impinge upon this said interface surface have an angle of incidence ($\alpha_i$) which is less than the angle of total reflection.

27. Device according to claim 26, wherein said means for preventing the formation of a light ray which has emanated from total reflection, on the surface forming the interface of said wall with the second side comprise a first flat surface forming the interface of said wall with said first side associated with a second convex surface forming the interface of said wall with said second side.

28. Device according to claim 27, wherein said second surface adopts a spherical cap form.

29. Device according to claim 27, wherein said second surface adopts a truncated form.

* * * * *